United States Patent [19]

Sakamoto et al.

[11] Patent Number: 4,641,092
[45] Date of Patent: Feb. 3, 1987

[54] ROTARY PROBE APPARATUS FOR DETECTING FLAWS IN A TEST OBJECT

[75] Inventors: Takahide Sakamoto; Tatsuo Hiroshima, both of Hyogo; Noriyuki Matsubara; Kenichi Miyata, both of Konomimachi, all of Japan

[73] Assignee: Sumitomo Metal Industries, Ltd., Osaka, Japan

[21] Appl. No.: 510,972

[22] Filed: Jul. 5, 1983

[30] Foreign Application Priority Data

Jul. 8, 1982 [JP] Japan .................................. 57-119421
Jul. 8, 1982 [JP] Japan .................................. 57-119422

[51] Int. Cl.[4] ..................... G01N 27/87; G01R 33/12; G01B 7/14
[52] U.S. Cl. .................................. 324/227; 324/236; 324/237; 324/240; 324/243; 324/261; 324/262
[58] Field of Search .............................. 324/219–221, 324/224–228, 232–243, 260, 261, 262

[56] References Cited

U.S. PATENT DOCUMENTS

| | | | |
|---|---|---|---|
| 3,582,771 | 6/1971 | Placke | 324/226 |
| 3,686,564 | 8/1972 | Mallick, Jr. et al. | 324/243 X |
| 3,746,972 | 7/1973 | Mandula, Jr. et al. | 324/262 X |
| 3,781,663 | 12/1973 | Abarotin et al. | 324/262 |
| 3,884,076 | 5/1975 | Studer | 324/226 X |
| 3,919,628 | 11/1975 | Mandula et al. | 324/261 |
| 4,084,136 | 4/1978 | Libby et al. | 324/238 |
| 4,101,832 | 7/1978 | Baker et al. | 324/238 X |
| 4,215,310 | 7/1980 | Schwerer, III | 324/238 X |
| 4,326,166 | 4/1982 | Pigeon et al. | 324/225 |
| 4,365,198 | 12/1982 | Toth | 324/226 |
| 4,461,995 | 7/1984 | Harris | 324/226 X |

OTHER PUBLICATIONS

"Multifrequency Eddy Current Inspection with Continuous Wave Methods", T. J. Davis, *Materials Evaluation*, Jan. 1980, pp. 62–68.

*Primary Examiner*—Reinhard J. Eisenzopf
*Assistant Examiner*—Warren S. Edmonds
*Attorney, Agent, or Firm*—Burns, Doane, Swecker & Mathis

[57] ABSTRACT

A flaw detection apparatus for detecting flaws at the outer surface of a product, such as a steel bar, wire or steel pipe, which is round in section and produced by the hot rolling, by use of a probe of non-contact type and rotating around the product to be inspected, the apparatus providing a means for suppressing vibrations of an object to be inspected, a means for measuring a distance (lift-off) between the object to be inspected and the probe, and a means for carrying out positional control on the basis of the detection result of the lift-off measurement so that the axis of rotation of probe is allowed to be coincident with the axis of object to be inspected. In a case of using the eddy current inspection for the flaw detection, two coils of standard comparison system are used and a mixed signal of a plurality of frequencies is applied to the coils so that a signal obtained by the probe coils suppresses the signal component caused by the lift-off variation and corrects the flaw signal caused by existence of the signal component, thereby eliminating the influence of lift-off variation and enabling measurement with high accuracy.

20 Claims, 20 Drawing Figures

(a)    (b)

4,641,092

ROTARY PROBE APPARATUS FOR DETECTING FLAWS IN A TEST OBJECT

BACKGROUND OF THE INVENTION

1. Field of the Invention

This invention relates to an apparatus which detects, by use of a non-contact type probe rotating around an object to be inspected, flaws on the outer periphery of a product, such as a steel bar, wire or steel pipe, round in section and manufactured by the hot rolling process.

2. Description of the Prior Art

Generally, a bar in coil or a wire of 50 mm or less in diameter is coiled immediately after rolled so that when flaw detection is performed in a cold condition, the coiled object need once be uncoiled for flaw detection and thereafter be recoiled. Therefore, it is efficient and desirable to detect flaws prior to coiling the object, in other words, in a hot condition just after the rolling process.

For inspecting the bar in coil or the like during the hot rolling process, an encircling coil type eddy current inspection method (electromagnetic induction flaw detection method) has hitherto been put into practice, which is a self-comparison method (obtaining self-impedance difference between two coils provided lengthwise of object to be inspected), whereby a short independent flaw, such as a scab or a roll mark, is detectable but harmful flaws existing lengthwise of the object are not so.

While, in order to detect flaws extending lengthwise of a long object, such as bar in coil, an eddy current inspection apparatus of rotary probe type has hitherto been put into practice, which rotates a probe coil around the bar in coil or the like at high speed in the cold condition, the apparatus picks up variation in impedance of the probe to detect the surface flaws, the variation in impedance being caused not only by the surface flaws on the object to be inspected but also by its quality, size and lift-off (a distance between the surface of object to be inspected and the probe coil), whereby when the size and quality of object to be inspected are different, the probe coil need be adjusted of its sensibility and it is important to scan the object keeping the lift-off constant.

The conventional eddy current inspection apparatus of rotary probe type used during the cold rolling keeps the lift-off constant by either one or combination of the following methods:

(1) to fix by pinch rolls the object to be inspected to thereby coincide the axis of object to be inspected with the axis of rotation of probe, and (2) to keep the probe in contact with the surface of the object to be inspected and follow the object.

FIG. 1 is a view exemplary of the eddy current inspection apparatus of rotary probe type, which adopts the above method (1). In detail, a rotary drum 202 driven by a motor 201 is disposed within a transfer zone of an object 10 to be inspected, two probe coils 203 are mounted at the inner surface of the rotary drum 202 and opposite to each other, at both axial sides of rotary drum 202 are disposed sleeves 204, 204 each of very hard metal and larger by about 0.1 to 0.2 mm in diameter than the object 10 to be inspected, the sleeves 204, 204 being concentric with the rotary drum 202, and pinch rolls 205, 205 holding the object 10 are mounted to the entrance and exit sides of the flaw detection apparatus in relation of being contactable with or movable away from the object 10 by air cylinders 206, 206 respectively, so that a motor 201 drives the rotary drum 202. Hence, the object 10 is rigidly fixed by the pinch rolls 205, 205 and guided by the sleeves 204, 204, whereby the object 10 to be inspected can be suppressed as much as possible of vibrations and eccentricity with respect to the rotary drum 202 and probe coils 203, 203.

Such flaw detection apparatus of rotary probe type, however, has many difficulties even when intended to be applied to the object to be inspected in the hot rolling, especially when applied in-process to the finish rolling or just after the finish rolling of bar in coil. In other words, since the rigidity of the object to be inspected under the hot rolling is small, it is impossible to rigidly hold the object by the pinch rolls because there is a fear of producing flaws on the surface of object and of deforming the object, and also the object cannot be suppressed completely of its vibrations, whereby the probes strike the object to be inspected to result in a fear of causing the flaws. Since guidance of the sleeves 204, 204 is impossible for the similar reason, it is difficult to coincide the axis of rotation of the drum 202 with the axis of object to be inspected, especially to obtain the axis thereof because the object is not round properly in section. The product of bar in coil or wire, even when uniform as well as different in the size, gradually varies in its pass line due to a different number of rolling times so that the axis of object to be inspected need be coincident every time with the axis of rotation of the probe.

Also, the aforesaid method (2) to keep the probe in contact with the surface of the object to be inspected and follow the object has a grave fear of causing flaws on the object in the hot rolling.

Furthermore, there are many factors, such as vibrations of a roll stand for the rolling or of a winding up mechanism, which induce vibrations on the object under the hot rolling, and the object itself is of less rigidity so as to have a grave fear of deflection between the pinch rolls, resulting in that the eddy current inspection apparatus of rotary probe type has been difficult to put into practice under the hot rolling.

Thus, the difficulty of keeping the lift-off constant will suggest the correction of detection signal by measurement of lift-off. Regarding the relation between the detection signal and the lift-off variation, there are two problems as follows:

(1) a signal caused by lift-off variation is superposed on the flaw signal so that both the signals are not distinguishable from each other, and (2) the lift-off variation changes the flaw signal itself.

Hence, the detection capability is remarkably deteriorated, whereby it is required to suppress a lift-off variation signal (a signal component caused by the lift-off variation) and also correct the flaw signal corresponding to the lift-off variation.

The phase discrimination method or the frequency discrimination method is well known as the aforesaid suppression of lift-off variation signal, the phase discrimination method phase-detecting the detection signal by the probe coils to thereby suppress noises and discriminate the flaw signal. FIGS. 2-(a) and -(b) are vector diagrams of signals from coils. In a case where the signal A caused by lift-off variation is different in phase from the flaw signal B as shown in FIG. 2-(a), the lift-off variation signal A intended to be suppressed is selected of the component of phase perpendicular to the direction of signal A (in the direction X) to thereby pick up the flaw signals B to be inspected. However, the flaw signal B and lift-off variation signal A do not always appear in different phase as shown in FIG. 2-(a), but often in a slight difference as shown in FIG. 2-(b), in which there is no effect in the suppression of lift-off variation signal A.

On the other hand, the frequency discrimination method is to suppress a not-desired signal (lift-off variation signal) by means of a difference between the same and the signal to be inspected (the flaw signal), but there is no effect for similar frequency components of both the signals.

For suppression of the signal difficult to suppress by such phase discrimination or frequency discrimination method, a multifrequency method is well known, which is to apply to an inspection coil currents of different frequencies in mixture, separately detect the signals each of frequency component, and compute a plurality of signal outputs obtained, thereby separating undesired signals.

FIG. 3 is a block diagram of the well-known multifrequency eddy current inspection apparatus used for the multifrequency method, in which reference numeral 211 designates an oscillator of frequency $f_1$ (e.g., 100 kHz), 212 designates an oscillator of that $f_2$ (e.g., 500 kHz), the outputs of both oscillators 211 and 212 being mixed in a mixer 213 and applied to detection coils 225 and 226 disposed in the self-comparison system through an impedance bridge 214 so that signals representing impedance variations in the coils 225 and 226 are given to tuned amplifiers 219 and 220 from the impedance bridge 214. The signals are amplified in synchronism with the frequencies $f_1$ and $f_2$ by the tuned amplifiers 219 and 220 respectively, the outputs therefrom, when viewed in the vector diagram, have the contents as shown in FIG. 2-(b). The outputs of tuned amplifiers 219 and 220 are given to phase sensitive detectors 221, 222 and 223, 224 respectively, the phase sensitive detector 221 or 223 being given, as the phase reference signal, the signal produced from an output of oscillator 211 or 212 given to a phase shifter 215 or 216, the output therefrom being given to a $\pi/2$ phase shifter 217 or 218 for shifting the phase by $\pi/2$ so that an output from shifter 217 or 218 is given to a phase sensitive detector 222 or 224 as the phase reference signal. The phase shifter 215 or 216, for example as shown in FIGS. 2-(a) and -(b), adjusts the signal A perpendicularly to the axis X, in other words, identically with the axis Y. Accordingly, a X-component (a resistance component) $X_1$ or $X_2$ of detection signal obtained by the frequency $f_1$ or $f_2$ is obtained by the phase sensitive detector 221 or 223 and a Y-component (a reactance component) $Y_1$ or $Y_2$ of the detection signal obtained by the frequency $f_1$ or $f_2$ is obtained by the phase sensitive detector 222 or 224.

Reference numeral 230 designates an analog signal-computing unit comprising phase rotators 231 and 232 for phase-rotating signals $X_2$ and $Y_2$ at an equal angle, amplifiers 223 and 234 for amplifying the outputs of phase rotators 231 and 232 in equal gains respectively, and differential amplifiers 235 and 236 which are given the outputs $X_2'$ or $Y_2'$ and $X_1$ or $Y_1$ of amplifiers 233 and 234 respectively, thereby obtaining the outputs x and y of differential amplifiers 235 and 236 respectively.

FIG. 4-(a) is a vector diagram of $X_1$ and $Y_1$, and FIG. 4-(b) is the same of $X_2$ and $Y_2$, in which the lift-off component $A_2$ shifts from the axis $Y_2$. The phase rotators 231 and 232 at the signal computing unit 230 are operated to rotate the phase and the amplifiers 233 and 234 are operated to equalize amplitude of signal $A_2$ to that of signal $A_1$, thereby obtaining signals $A_2'$ and $B_2'$ as shown in FIG. 4-(c) and giving them to the differential amplifiers 235 and 236 respectively. Since the differential amplifiers 235 and 236 output a difference between two input signals, a difference $A_1-A_2'$ between the lift-off components becomes a signal "a" of minute level as shown in FIG. 4-(d) and when the flaw signal exists, a difference "b" between $B_1$ and $B_2$ (expressed in vector) is obtained.

On the hand, a change in the flaw signal following the lift-off variation in the aforesaid item (2), as shown in FIG. 5, abruptly attenuates following an increase of lift-off, whereby in condition of lift-off variation, some means should be taken to detect the lift-off and correct the signal output.

The multifrequency method can almost suppress the signal caused by the lift-off variation, but it is extremely difficult to accurately detect the lift-off variation and correct the flaw signal. The first reason is as follows. It is difficult to detect the lift-off variation with accuracy. For example, it is impossible to measure the lift-off variation by a distance detector which is provided independently from the probe so as to detect the distance between the probe coil and object to be inspected. A contact system with a differential transformer or the like can not follow at its contact end after the object moving at high speed. A measuring device of eddy current type, when in use, is affected by flaws or the like, the detection result becoming a mixture of factors of both the lift-off and flaws. Second reason is as follows. The lift-off variation is divided roughly into two forms which should be corrected separately from each other. FIGS. 6-(a) and -(b) are schematic views explanatory of configurations of lift-off variation in the self-comparison system when the object 240 to be inspected is round in section like bars in coil, FIGS. 7-(a) and -(b) are schematic views explanatory of the same of self-comparison system when the object 240 is a plate-like object, such as a steel plate. FIGS. 6-(a) and 7-(a) show the object 240 moving as a whole toward the probe coils 225 and 226, FIGS. 6-(b) and 7-(b) show the object 240 moving other directions, and FIGS. 8-(a) and -(b) show detection patterns of flaw signal in FIGS. 6-(a) and 7-(a) and FIGS. 6-(b) and 7-(b) respectively. The flaw signal, which usually appears in origin symmetry as shown by the solid line in FIGS. 8-(a) and -(b), is expanded while being kept in origin symmetry as shown by the broken line in FIG. 8-(a) when the object 240 moves as a whole uniformly toward the probe coils 225 and 226, and is distorted not in origin symmetry as shown by the broken line in FIG. 8-(b) when the object 240 moves other directions. In a case where the flaw detection is carried out by the self-comparison method which disposes two probe coils 225 and 226 close to each other and picks up the impedance difference in comparison with the existing of flaws on the object 240 at the portion thereof corresponding to the probe coils 225 and 226 in close contact with each other, when the object 240 moves uniformly toward the probe coils 225 and 226 as shown in FIGS. 6-(a) and 7-(a), the lift-off of each probe coil 225 and 226 becomes equal to keep the symmetry of detection pattern of flaw signal, thus merely expanding (or diminishing) the signal. On the other hand, when the object 240 moves other directions, the lift-off of one probe coil 225 is reduced to be a pattern in the first quadrant in FIG. 8-(b) and that of another probe coil 226 is enlarged to be a pattern in the third quadrant in the same figure. Thus, the two kinds of signals cannot be similarly corrected merely by measuring the distance between the probe coils and the object, thereby requiring to pick up configuration of each lift-off variation and correct the signal.

Generally, in order to be less affected by the lift-off variation, the probe type eddy current inspection method employs the self-comparison method, so that when a lift-off value for one probe coil just above the flaw is different from that for the other in the same condition, a distortion is produced as shown in FIG. 8-(b). Also, the lift-off variation signal detected by the multifrequency method is not clarified of the absolute value of lift-off because the signal is a difference in lift-off between both the coils.

OBJECTS OF THE INVENTION

In the light of the aforesaid problems, this invention has been designed.

A first object of the invention is to provide a flaw detection apparatus which is capable of detecting flaws on the outer peripheral surface of a hot rolled object round in section under less influence of lift-off variation of a probe as much as possible.

A second object of the invention is to provide a flaw detection apparatus which is capable of detecting the flaws on a hot rolled object round in section with accuracy and without injuring the outer peripheral surface of the object.

A third object of the invention is to provide a flaw detection apparatus which is capable of detecting the flaws with accuracy and without being affected by vibration of an object to be inspected.

A fourth object of the invention is to provide a flaw detection apparatus which is capable of detecting flaws with accuracy by eliminating a factor of causing a local lift-off variation not completely absorbed even when the center of the rotary member carrying the probe is controlled to be aligned with the center of the object to be inspected.

A fifth object of the invention is to provide an eddy current system flaw detection apparatus which is capable of detecting flaws at the outer peripheral surface of a hot rolled object round in section under less influence of lift-off variation of the probe as much as possible.

A sixth object of the invention is to provide an eddy current system flaw detection apparatus which is capable of detecting flaws at the outer peripheral surface of a hot rolled object round in section under less influence of lift-off variation of the probe as much as possible, thereby performing the quantitative evaluation of detection with accuracy.

The above and further objects and features of the invention will more fully be apparent from the following detailed description with accompanying drawings.

DETAILED DESCRIPTION OF THE INVENTION

Figure 9:
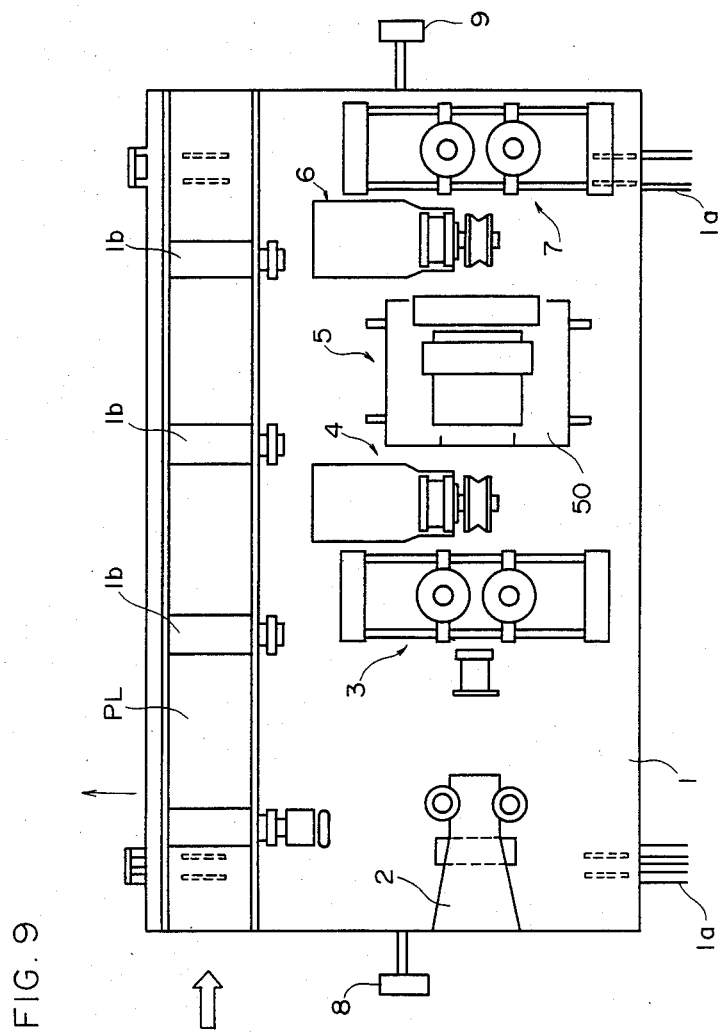
FIG. 9 is a plane view showing a layout of mechanical portions as a whole at a flaw detection apparatus of the invention.

The arrangement of mechanical components of the flaw detection apparatus of the invention will be shown in FIG. 9, in which reference PL designates a pass line on which an object to be inspected and discharged from a final rolling machine is transferred in the direction of the unshaded arrow. A truck 1 loading the detection apparatus and others is movable on rails 1a, 1a extending horizontally and perpendicularly to the pass line PL. In the state as shown, the flaw detection apparatus escapes at the center line thereof from the pass line PL to thereby convey the object on rolls 1b, 1b provided at the left side and toward the downstream side in the object conveying direction on the truck 1. While, in a case of carrying out the flaw detection, a drive means (not shown) moves the truck 1 as a whole leftwardly (in the direction of the solid arrow in FIG. 9) with respect to the downstream direction, so that the object to be inspected is adapted to pass along the center line of detection apparatus, in other words, the pass line PL of object to be inspected coincides with the center line of the same.

On the truck 1 are disposed a guide tube 2, pinch roll assemblies 3 and 4, a probe rotation unit 5, and pinch roll assemblies 6 and 7 in the order from the upstream side in the object conveying direction.

The guide tube 2 is upstream-expanded-trumpet-shaped and provided on the truck 1 at the upstream side thereof and in parallel to the pass line PL, and is about level at the axis with the axis of rotation of probe rotation unit 5 to be discussed below.

At the downstream side of guide tube 2 are provided the horizontal pinch roll assembly 3 in which rolls are juxtaposed horizontally, vertical pinch roll assembly 4 in which rolls face vertically each other, and probe rotation unit 5, and then the vertical pinch roll assembly 6 and a horizontal pinch roll assembly 7, in the order from the upstream side to the downstream.

Figure 10:
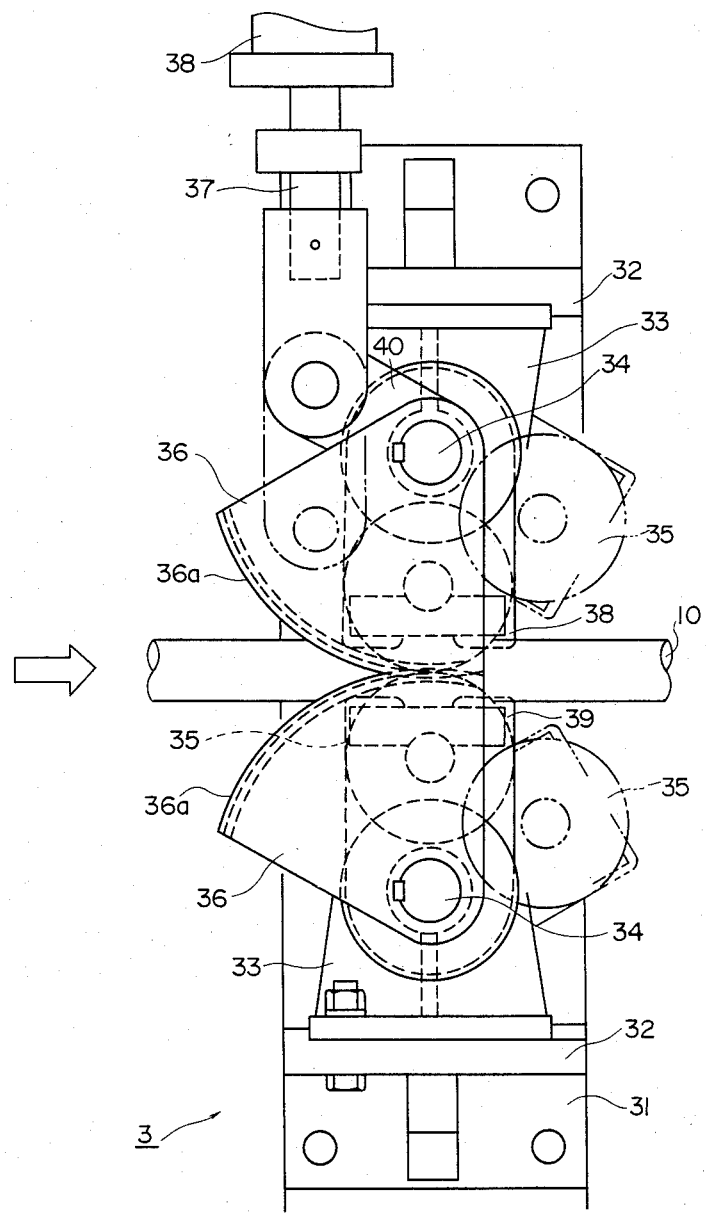
FIG. 10 is a plane view of a horizontal pinch roll assembly.
Figure 11:
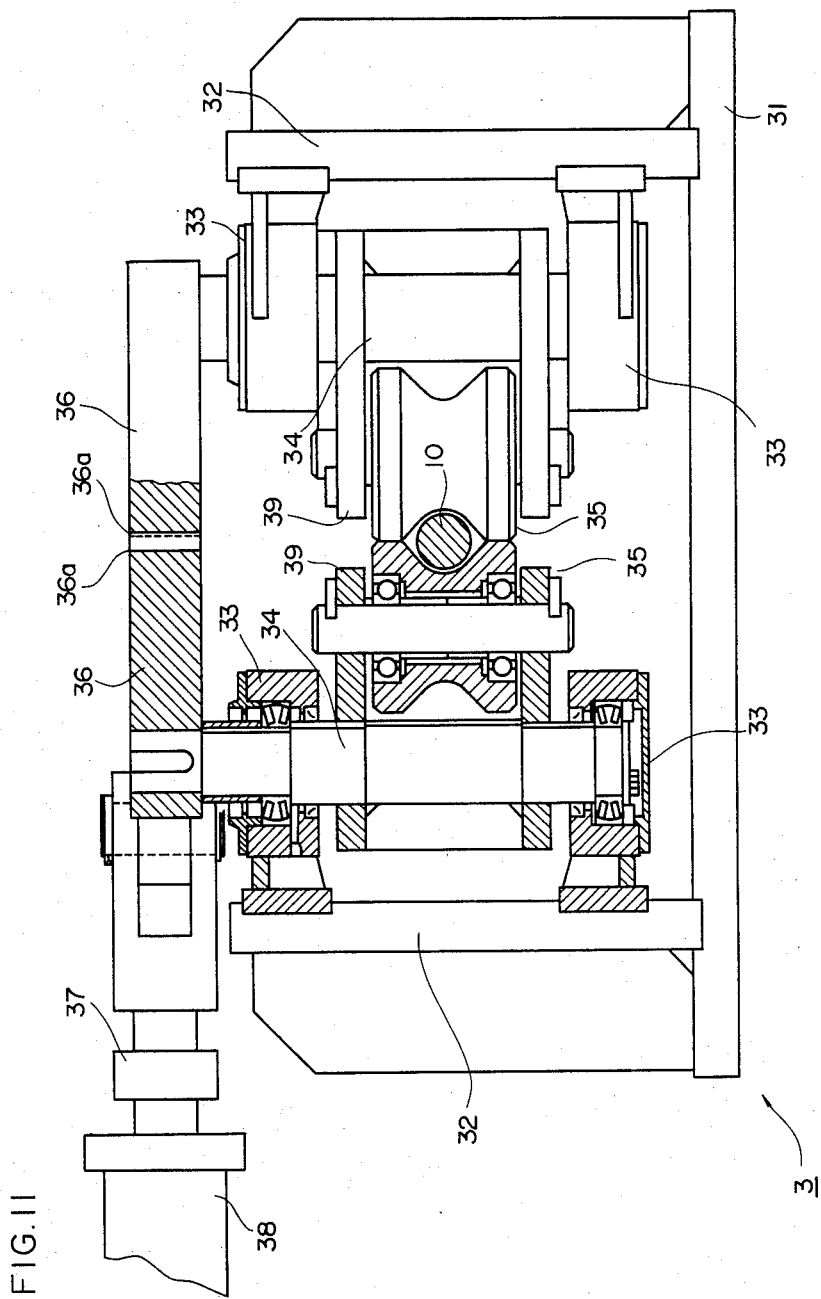
FIG. 11 is a partially cutaway sectional view of the horizontal pinch roll assembly when viewed from the upstream side in the transfer direction of the object to be inspected.

Referring to FIGS. 10 and 11, support plates 32, 32 are provided upright and opposite to each other on the upper surface of a base 31 at both end portions thereof perpendicularly to the pass line PL, bracket members 33, 33 are provided at the upper and lower portions on the opposite surfaces of support plates 32 respectively, and support shafts 34 are supported rotatably between the upper and lower bracket members 33 at the support plates 32 respectively, the support shafts 34 carrying at the portions between the upper and lower bracket members 33, 33 holders 39 vertically carrying rolls 35 pivotally supported thereto, the rolls 35 having therebetween a caliber portion (a pass) slightly larger in diameter than the object 10 to be inspected, thereby suppressing vibrations thereof at the caliber portion. Sector gears 36, 36 are mounted to the upper ends of support shaft 34, 34 respectively and have toothed portions 36a, 36a in mesh with each other at the center between the support plates 32, 32, one sector gear 36 rotating following the rotation of the other so that the supporting shafts 34, 34 rotate to allow the rolls 35, 35 to rotate respectively. One support shaft 34 at the left side toward the downstream side carries an arm 40 at one end thereof, the arm 40 pivotally supporting at the other end thereof a piston rod 37 of an air cylinder 38 so that the piston rod 37 moves forward to rotate the support shaft 34 to thereby rotate one roll 35 thereon in the downward direction, at which time one sector gear 36 rotated through the one roll 35 rotates the other sector gear 36 so that the other roll 35 rotates in the downstream direction. In brief, the piston rod 37 advances to rotate both the rolls 35, 35 downstream in the conveying direction of object 10 to be inspected. On the other hand, when the piston rod 37 retracts, the support shaft 34 rotates upstream in the conveying direction of object 10 to rotate one roll 35 upstream and the other roll 35 rotates upstream through the sector gears 36, 36 in mesh with each other. In the state where the piston rod 37 retracts as shown by the solid line in FIG. 10, both the rolls 35, 35 are in contact with each other to hold the object 10 in the caliber portion under condition of balancing with the air pressure in the air cylinder 38. However, in case that the object 10 to be inspected comes into press-contact with the rolls 35, 35 and drives them so that the contact force overcomes the air pressure in the air cylinder 38, the one roll 35 rotates downstream to allow the piston rod 37 to advance, whereby both the rolls 35, 35 turn to the position shown by the two-dot-chain line in FIG. 10, thus releasing the object 10.

The horizontal pinch roll assembly 7 positioned downstream of the probe rotation unit 5 is constructed as the same as the pinch roll assembly 3. While, the vertical pinch roll assemblies 4 and 6 each comprise two rolls disposed vertically. Rolls 35 at the respective pinch roll assemblies 3, 4, 6 and 7 are adapted to release or hold the object 10 to be inspected by each air cylinder 22 actuated by signals of hot material detectors 8 and 9 provided at the upstream and downstream sides of truck 1, the signals of hot material detectors 8 and 9 serving to advance or retract probes 21, 21 at the probe rotation unit 5 to be discussed below.

Figure 12:
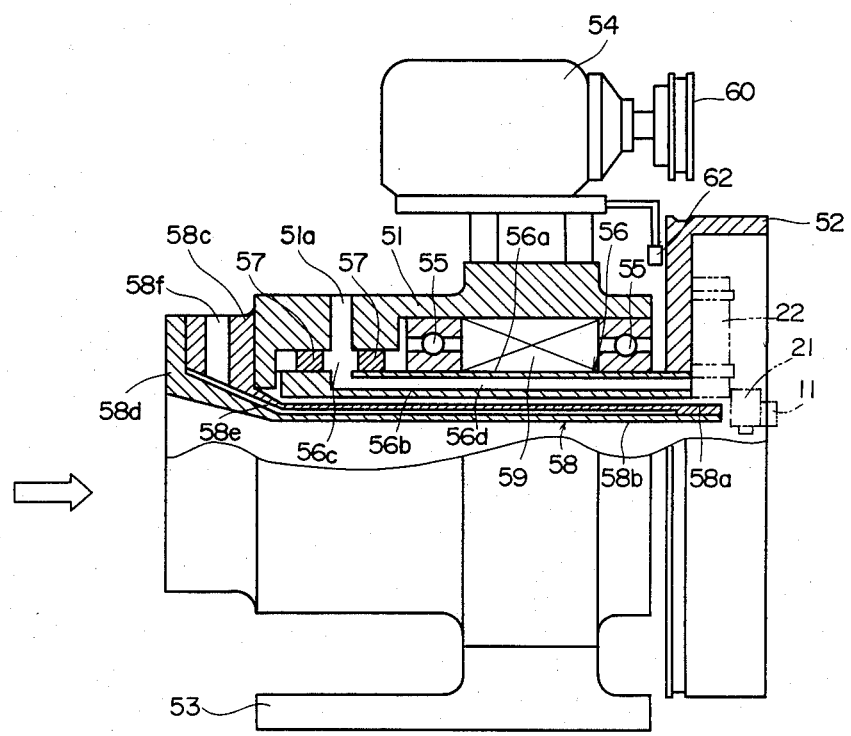
FIG. 12 is a partially cutaway side view of a probe rotation unit at the apparatus of the invention.

Referring to FIG. 12, the probe rotation unit 5 is mounted on a support 53 provided vertically movably to a base 50 which is mounted on the truck 1 in relation of being movable perpendicularly to the conveying direction of object 10 to be inspected.

At the upper surface of support 53 is fixed a cylindrical housing 51, and at the upper surface thereof is mounted a motor 54 whose output shaft is directed downstream in the conveying direction of object, and a pulley 60 is mounted to the utmost end of the output shaft and a V-belt 61 (see FIG. 14) is carried across the pulley 60 and the outer periphery of a rotary drum 52 at the housing 51 side, the rotary drum 52 being mounted to the dwonstream side of housing 51, so that the rotation of motor 54 is transmitted to the rotary drum 52 through the V-belt 61. The rotary drum 52 is short cylindrical, covered at the upstream side end by a side plate open at the center, mounted concentrically and rotatably to the housing 51 at the downstream side thereof, and carries at the inside of side plate a flaw detecting probe 21 and air cylinders 22, 22 for advancing or retracting the probe 21 respectively (see FIG. 13 as to these components).

An air-flow duplex tube 56 is mounted in the housing 51 through bearings 55, 55 and comprises an outer tube 56a and an inner tube 56b concentrically connected therewith through spacers (not shown), the upstream side ends of outer tube 56a and inner tube 56b being closed therebetween to form an air conduit 56d with the inner periphery of outer tube 56a and the outer periphery of inner tube 56b. The air conduit 56d extends at the downstream side end into the rotary drum 52 and the side plate thereof is fixed to the downstream side end of outer tube 56a, thereby allowing the airflow tube 56 to rotate integrally with the rotary drum 52. An air inlet 56c is provided at the periphery of the upstream side end portion of outer tube 56a and an air inlet 51a is open at the upper portion of housing 51 opposite to the air inlet 56c. Sealing members 57, 57 are fitted on the outer tube 56a at the upstream and downstream sides of air inlet 56c respectively, thereby sealing between the inner periphery of housing 51 and the outer periphery of outer tube 56a. Thus, compressed air is taken in through the air inlet 51a and passes through the air inlet 56c and air conduit 56d, thereby being fed from the downstream side end thereof into the air cylinders 22, 22 in the rotary drum 52 and used as air for driving the air cylinders 22, 22.

A guide tube 58 is fitted into the air-flow tube 56 and comprises an outer sleeve 58a and an inner sleeve 58b fitted concentrically therein, the outer sleeve 58a providing at the upstream side end a flange 58c fixed to the upstream side end face of housing 51, and the inner sleeve 58b also providing at the upstream side end a flange 58d connected to the flange 58c. Between the outer sleeve 58a and the inner sleeve 58b is provided a water passage 58e and a water inlet 58f formed at the flange 58c of outer sleeve 58a, so that a cooling water is taken in from the water inlet 58f and flows in the water passage 58e, thereby cooling the guide tube 58 as a whole and being discharged to the exterior through an outlet (not shown). Thus, the object 10 to be inspected perforates through the guide tube 58 from the upstream side toward the downstream, the air-flow tube 56 rotating around the guide tube 58. A rotary transformer 59 is provided opposite to the outer periphery of air-flow tube 56 and the inner periphery of housing 51 to thereby serve to send or receive signals with respect to a probe 21 within the rotary drum 52.

Within the rotary drum 52 are mounted the probe 21, air cylinders 22, 22 for retracting the probe 21, and connecting members 24, 24 for connecting the air cylinders 22 and probe 21.

Figure 13:
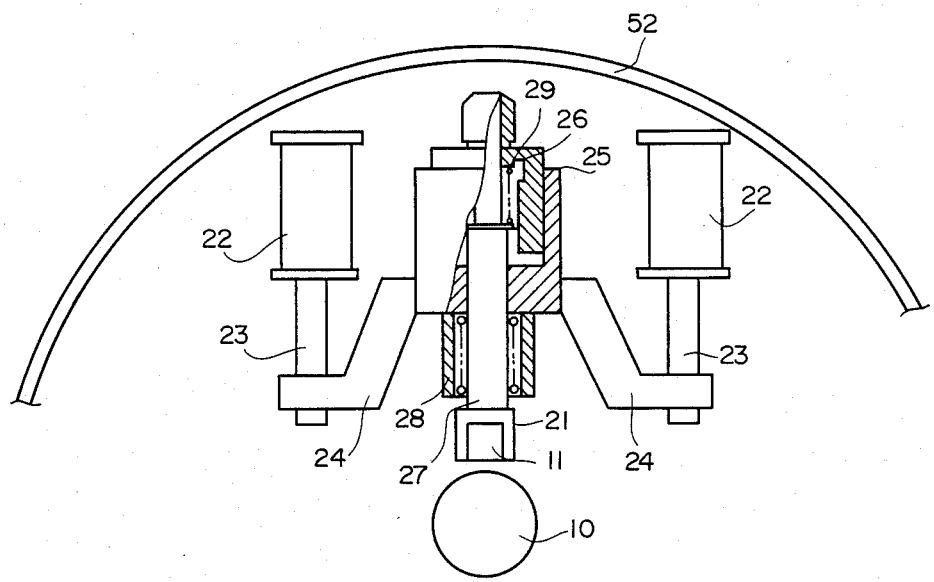
FIG. 13 is a partially cutaway schematic sectional view of a rotary drum at the apparatus of the invention.

FIG. 13 is a partly cutaway schematic sectional view of the rotary drum 52 when viewed from the downstream side in the conveying direction of object 10 to be inspected, in which the probe 21 is provided at the utmost end of a support shaft 27 toward the center of rotary drum 52, and has a distance sensor 11 which detects a distance between the probe 21 and the outer peripheral surface of object 10 so as to avoid electromagnetic interference therebetween, the support shaft 27 extending radially inwardly of rotary drum 52 and fitted at the root slidably into a cylindrical casing 25 the axis of which extends radially of rotary drum 52. An adjusting cylinder 26 is screwably fitted into the casing 25 at the portion thereof radially outward of rotary drum 52 and the support shaft 27 perforates the adjusting cylinder 26 and the casing 25, and is provided at the outer end with a lock. A compression spring 29 is interposed between the inner bottom of adjusting cylinder 26 and a spring seat formed at the support shaft 27, thereby biasing the support shaft 27, in turn the probe 21, toward the center of rotary drum 52, so that the adjusting cylinder 26 is rotationally operated to move the probe 21 radially of rotary drum 52, thereby carrying out positional adjustment of probe 21 corresponding to variation in diameter of object 10. Also, a slide bearing 28 is mounted at the surface of casing 25 facing the center of rotary drum 52 and fitted onto the support shaft 27, thereby facilitating axial movement of support shaft 27, in turn the probe 21, and eliminating the laterally swinging motion of the same.

The air cylinders 22, 22 are mounted to the rotary drum 52 and disposed at both sides of support shaft 27 perpendicularly to the axis thereof, the piston rods 23, 23 extending in parallel to the support shaft 27 and moving toward or away from the center of rotary drum 52, the connecting members 24, 24 being mounted at one ends thereof to the utmost ends of piston rods 23 and at the other ends to both lateral sides of casing 25 respectively. Thus, in order to prevent collision of probe 21 with the object 10 when its fore end or rear end passes through the rotary drum 52, the piston rods 23, 23 at the air cylinders 22 are retracted, whereby the casing 25 and support shaft 27 as a whole move away from the object 10 and escape therefrom.

Figure 14:
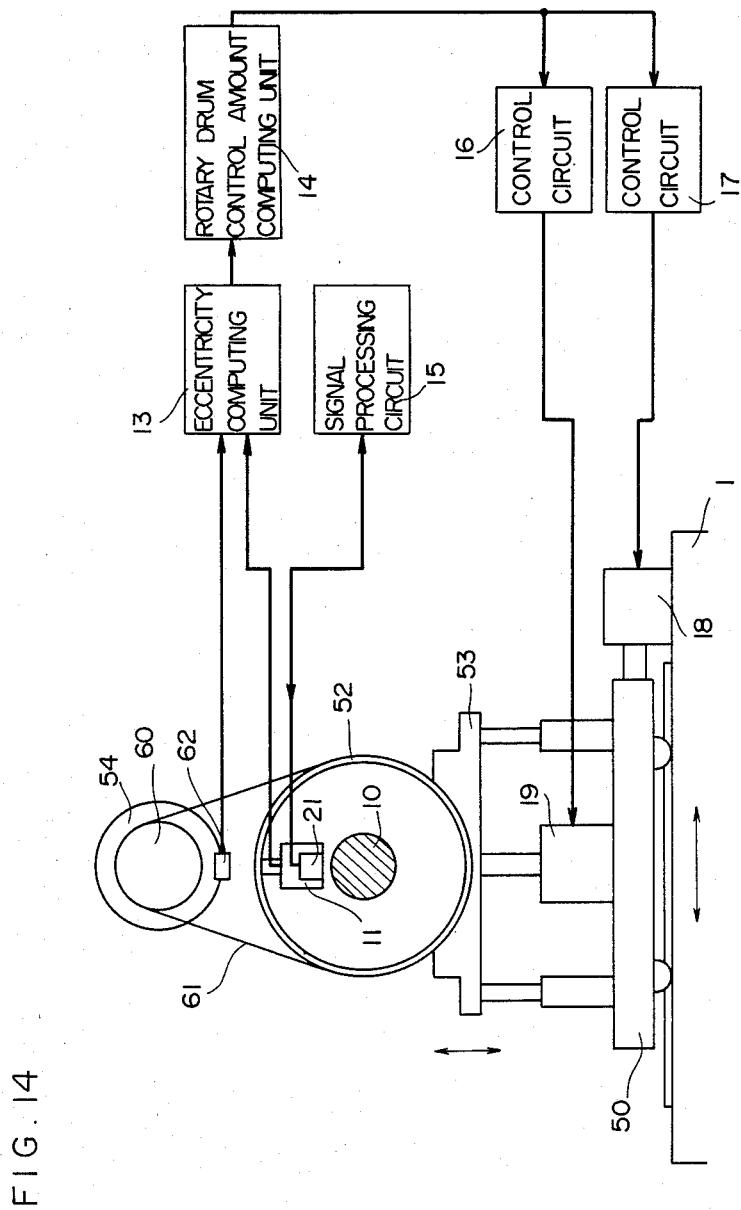
FIG. 14 is a view exemplary of a probe rotating unit together with its control system of the invention.

Next, referring to FIG. 14, the support 53 is mounted vertically movably on the base 50 movable perpendicularly to the conveying direction of object 10, a motor 19 for moving the support 53 up and down is mounted on the base 50, and a motor 18 for moving the base 50 is provided on the truck 1.

A detection signal of distance sensor 11 of eddy current type for detecting a distance between the probe 21 or a distance sensor 11 and the outer periphery of object 10, is given into a computing unit 13 for computing the eccentricity between the axis of object 10 and the axis of rotation of probe 21. The eccentricity computing unit 13 comprises, for example, a microcomputer, and analog/digital-converts a detection signal from the distance sensor 11 and fetches it. At the outer surface of the side plate at the rotary drum 52 are applied magnetic marks indicating the reference position and every fixed angle and at a frame for the motor 54 is mounted a rotary position detecting sensor 62 using a magnetic sensor detectable of the magnetic marks and disposed opposite thereto, so that the detection signal of rotary position detecting sensor 62 is given to the eccentricity computing unit 13. The eccentricity computing unit 13 stores an input given from the distance sensor 11 in connection with the input given from the rotary position sensor 62, so that a distance between the distance sensor 11 or probe 21 and the object 10 with respect to each rotary position, is computed on an average as to a plural number of rotations of rotary drum 52. The reason for such averaging process is as follows: a signal caused by eccentricity between the axis of object 10 and the axis of rotation of probe 21, changes to draw a curve of a fixed frequency having one cycle period of a time corresponding to one rotation of probe 21, but random signals caused by vibrations of object 10 also are superposed on the detection signal of distance sensor 11, the random signals being removed by averaging the detection signals of distance sensor 11 by the signals corresponding to a plural number of rotations of rotary drum 52, thereby making it possible to fetch only the signal caused by the eccentricity.

The result of computation by the eccentricity computing unit 13 has been given into a rotary drum control amount computing unit 14, so that the eccentricity between the center of rotary drum 52 and the axis of object 10 to be inspected is computed of its vertical component and its horizontal component perpendicular to the object conveying direction, the driving signals are output to a control circuit 16 for the motor 19 and to a control circuit 17 for a motor 18 so as to rotate the motors 19 and 18 normally or reversely to thereby move the rotary drum 52 only to an extent of each computed amount, and the support 53 and base 50 are moved vertically and laterally respectively to change the rotary drum 52 in position, whereby the axis of rotation of probe 21 is adapted to coincide with the axis of object 10 to be inspected.

The rotary drum control amount computing unit 14 may comprise the same computer as for the eccentricity computing unit 13, or comprise a micro processor.

Numeral 15 in FIG. 14 designates the signal processing circuit (shown in FIG. 17) for the detection signal of probe 21.

Figure 15:
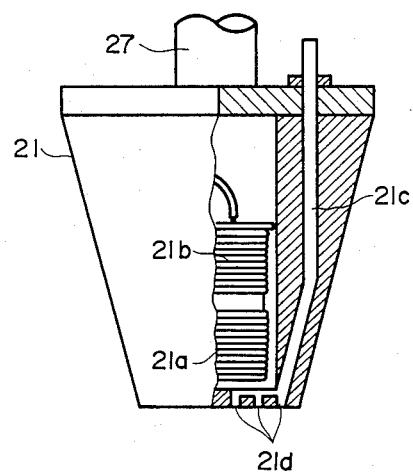
FIG. 15 is a partially cutaway elevation exemplary of a probe.

Referring to FIG. 15, an embodiment of probe 21 applicable to the flaw detection apparatus of the invention is shown. The probe 21 is frustoconical and mounted to the support shaft 27 in relation of keeping the smaller diameter portion below, and also has in its cavity coils 21a and 21b and at its peripheral wall an air inlet 21c through which compressed air is taken in, the air inlet 21c connecting with a plurality of air jet outlets 21d open at the bottom opposite to the object 10 to be inspected, and with the air-flow tube 56d or a compressed air supply tube separate therefrom, so that air of constant pressure and quantity is blown out through the air jet outlets 21d. In a case of using the probe 21 of such construction, the control by alignment of probe 21 with the object 10 also can eliminate the remaining local lift-off variation. In other words, when the peripheral surface of object 10 approaches the probe 21, the pressure at each air jet outlet 21d rises, whereby the probe 21 in itself moves away from the object 10. Conversely, when the pressure lowers, the probe 21 moves toward the object 10.

In addition, the probe 21 at the flaw detection apparatus of the invention is not limited to the above.

Figure 16:
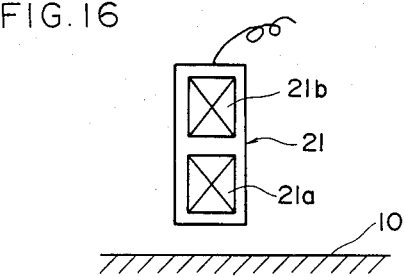
FIG. 16 is a view exemplary of arrangement of probe coils.

Next, explanation will be given on a signal processing system. The signal processing system depends on the aforesaid multifrequency method and also probe coils 21a and 21b are disposed in the standard comparison system, in which one probe coil 21a is positioned toward the object 10 and the other probe coil 21b away therefrom and free from electromagnetic connection with the same as shown in FIG. 16.

Figure 1:
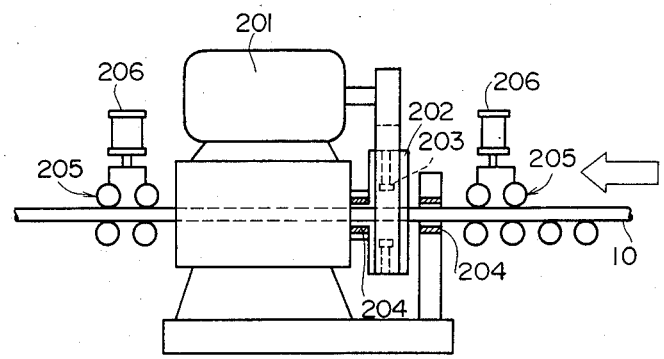
FIG. 1 is an elevation exemplary of a conventional eddy current inspection apparatus of rotary probe type for an object in the cold rolling.
Figure 2:
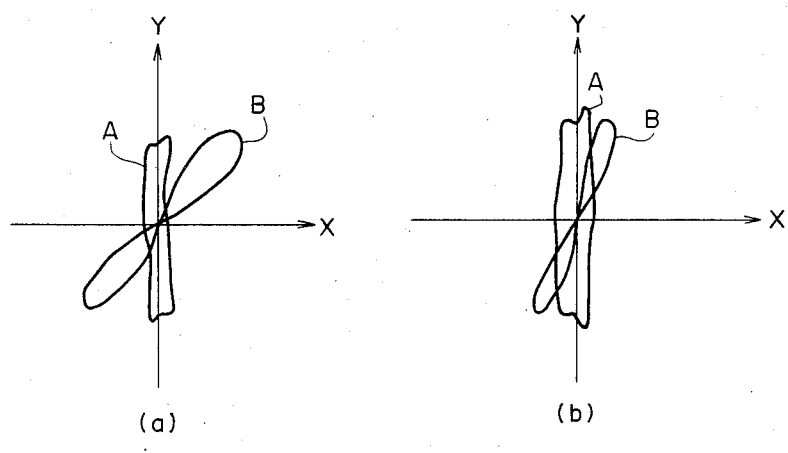
FIG. 2 is a vector diagram showing a relation between flaw signals and lift-off variation signals.
Figure 3:
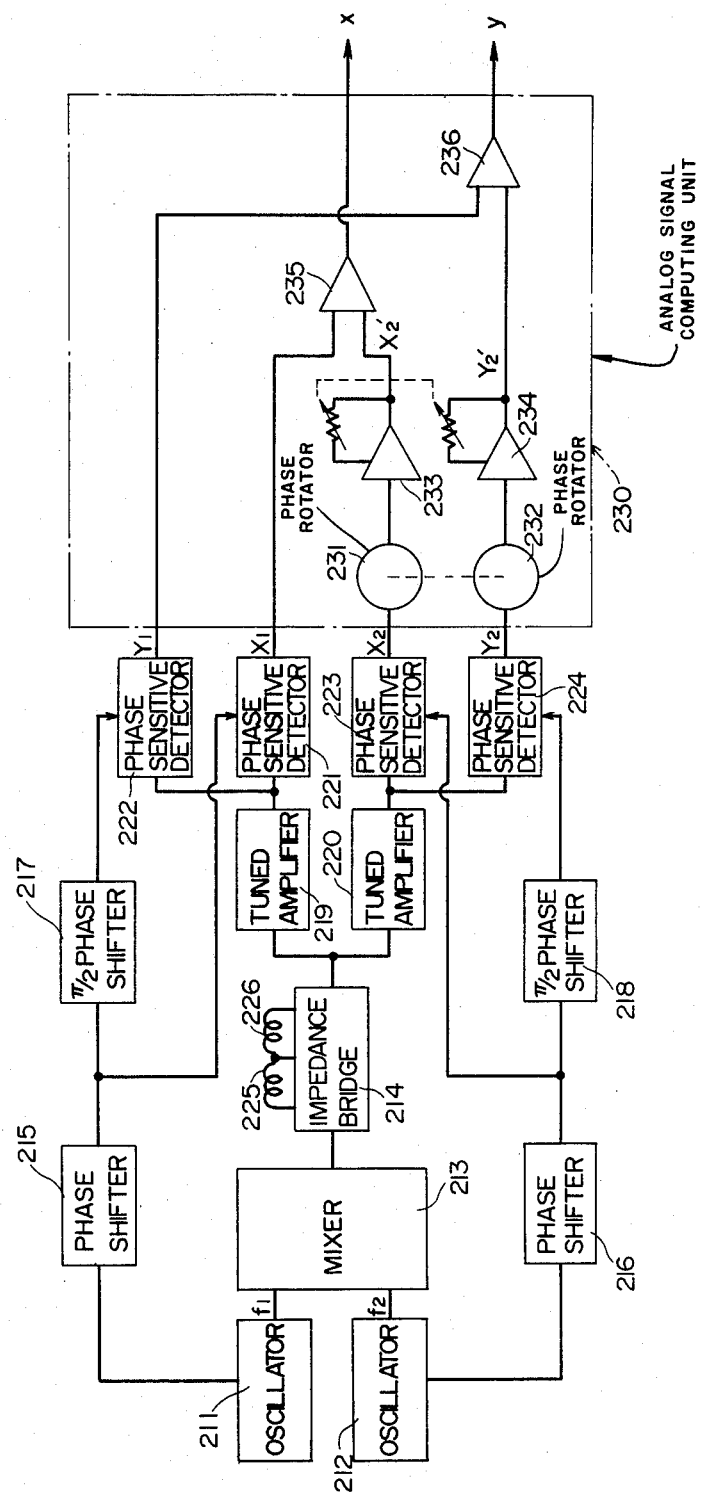
FIG. 3 is a circuit diagram of circuitry of a conventional multifrequency eddy current inspection apparatus.
Figure 4:
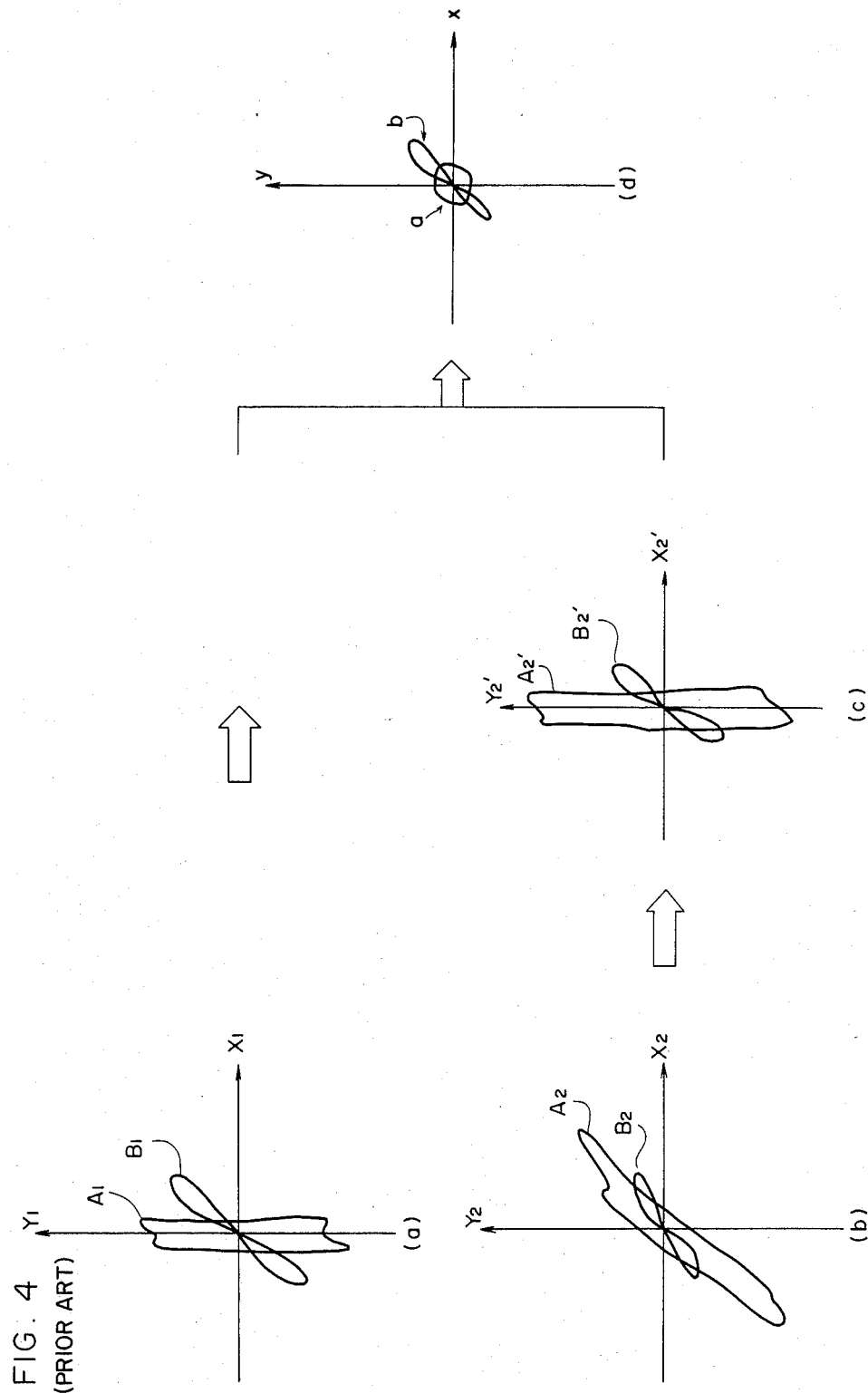
FIG. 4 is a vector diagram explanatory of operation of the apparatus in FIG. 3.
Figure 5:
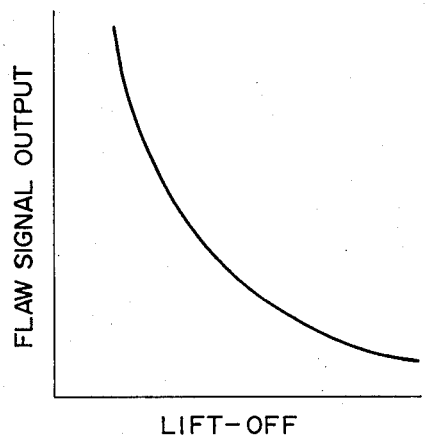
FIG. 5 is a graph showing a relation between the lift-off and the flaw signal output.
Figure 6:
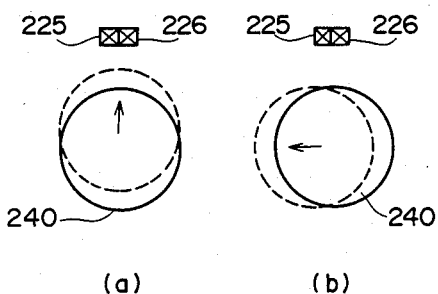
FIGS. 6 and 7 are schematic views showing relations between the probe coil and the object to be inspected.
Figure 7:
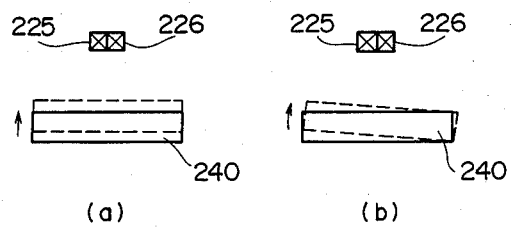
Figure 8:
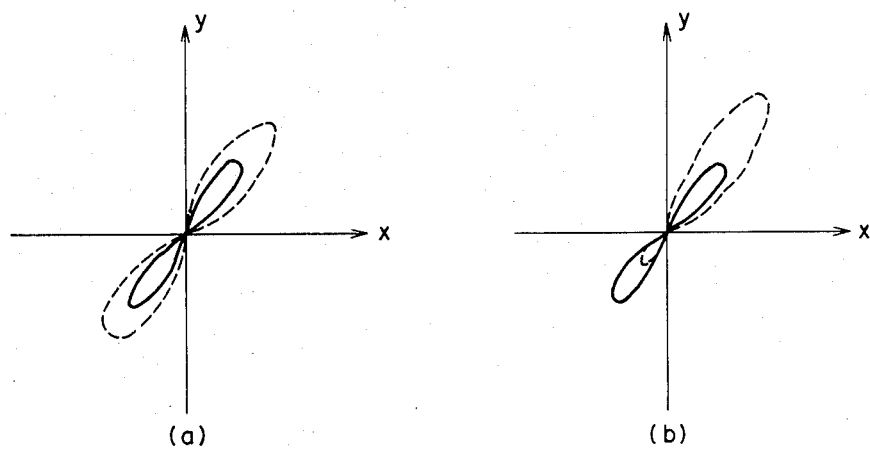
FIG. 8 is a vector diagram of the flaw signal.
Figure 17:
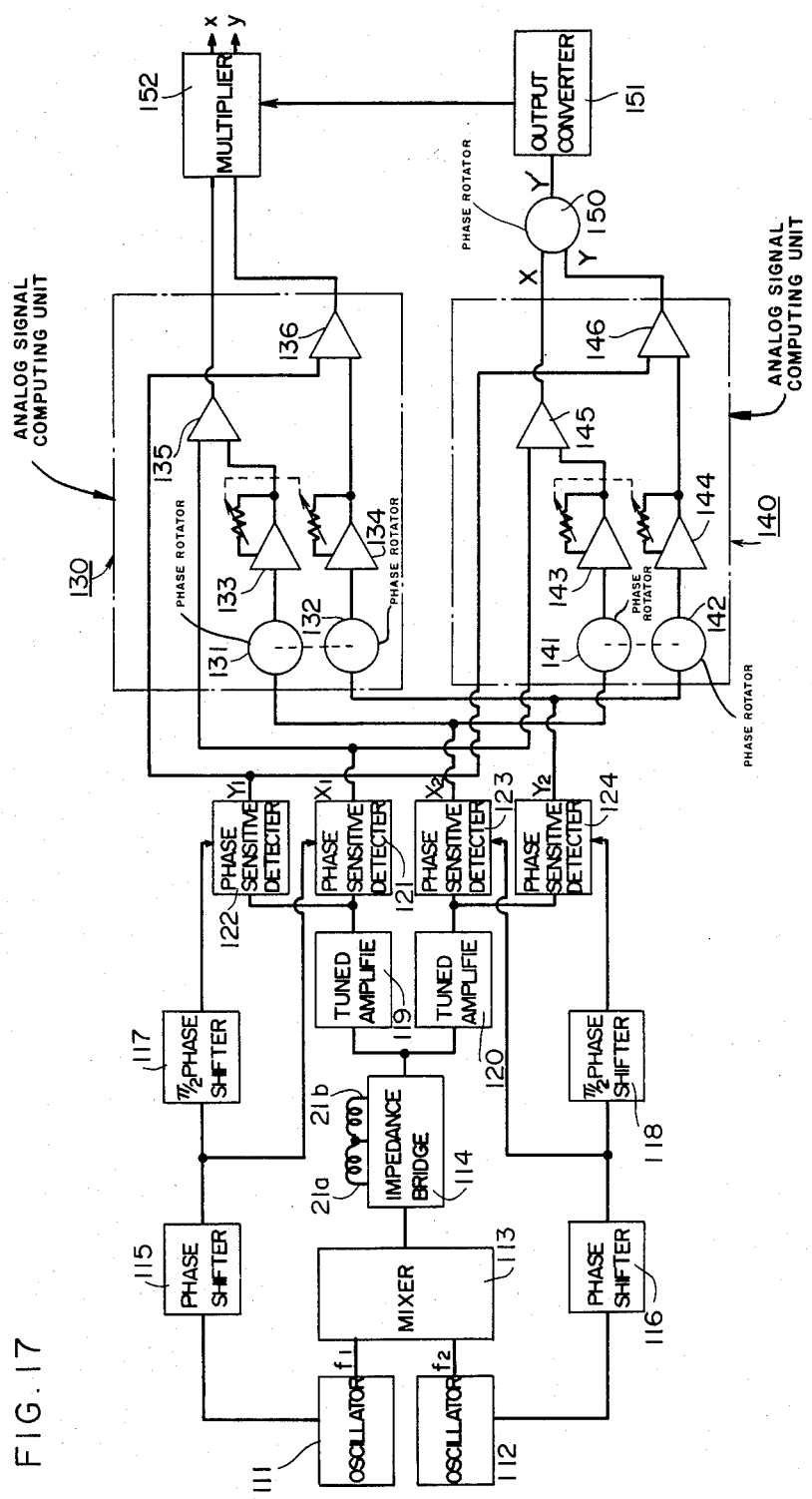
FIG. 17 is a block diagram of a signal processing circuit at the apparatus of the invention.

Referring to FIG. 17, outputs of oscillators 111 and 112 are mixed by a mixer 113 and applied to the probe coils 21a and 21b through an impedance bridge 114 so that the signal representing its impedance change is given from the impedance bridge 114 to tuned amplifiers 119 and 120, thereby being tuned-amplified. The outputs of tuned amplifiers 119 and 120 are given to phase sensitive detectors 121, 122 and 123, 124 respectively, the phase sensitive detectors 121 and 123 being given the phase reference signals obtained by giving outputs of oscillators 111 and 112 to the phase shifters 115 and 116 respectively, and also the phase sensitive detectors 122 and 124 being given outputs of phase shifters 115 and 116 through $\pi/2$ phase shifters 117 and 118 respectively. Output signals of phase sensitive detectors 121, 122, 123 and 124 are given to a first analog signal computing unit 130 and also to a second analog signal computing unit 140 respectively. The signal computing units 130 and 140 comprise phase rotators 131, 132 and 141, 142, amplifiers 133, 134 and 143, 144, and differential amplifiers 135, 136 and 145, 146, so that on the basis of the FIG. 3 circuit the first signal computing unit 130 as aforesaid can essentially fetch only the flaw signal by suppressing the lift-off variation signal. While, the second signal computing unit 140 as the same as the first one operates the phase rotators 141 and 142 to rotate in phase and the amplifiers 143 and 144 are operated to equalize the amplitude, in other words, to obtain a relation of $B2'=B1$ as shown in FIG. 4, so that when the flaw signal exists, the difference: $B1-B2'$ is of a minute level to thereby obtain the lift-off variation signal shown in FIG. 18-(a).

Figure 18:
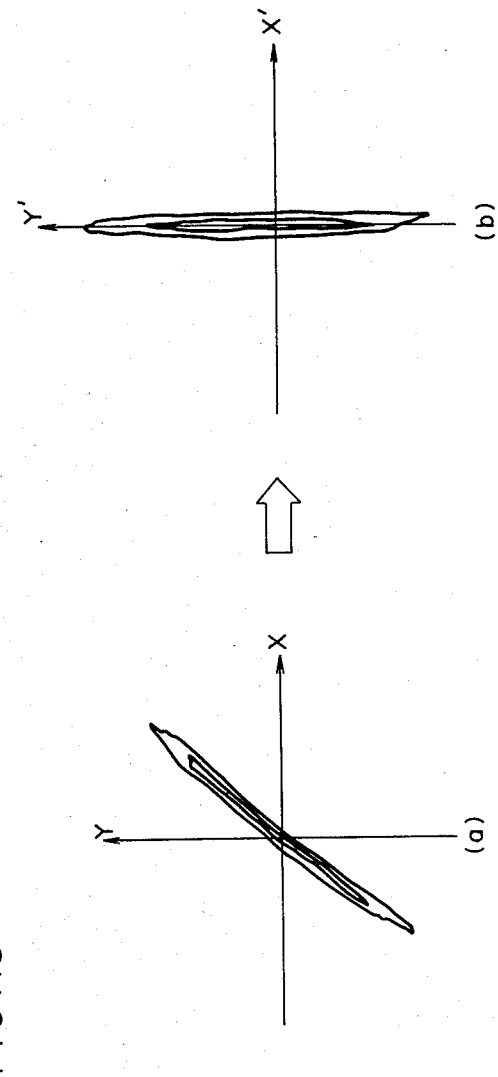
FIG. 18 is a vector diagram of a lift-off variation signal.

The output of second signal computing unit 140 is given to a phase rotator 150, in which when inputs X and Y each are rotated at a given angle, the lift-off component can be identical with the axis Y as shown in FIG. 18-(b), thereby enabling the output Y' to be used directly as a lift-off value in the scalar quantity.

Figure 19:
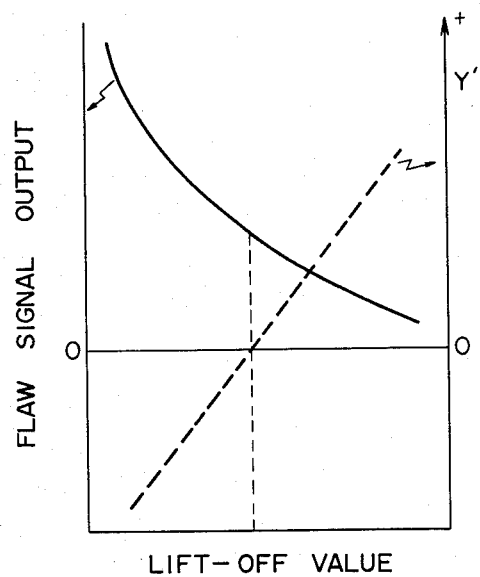
FIG. 19 is a graph showing a relation between a lift-off value, a flaw signal output and a component Y'.
Figure 20:
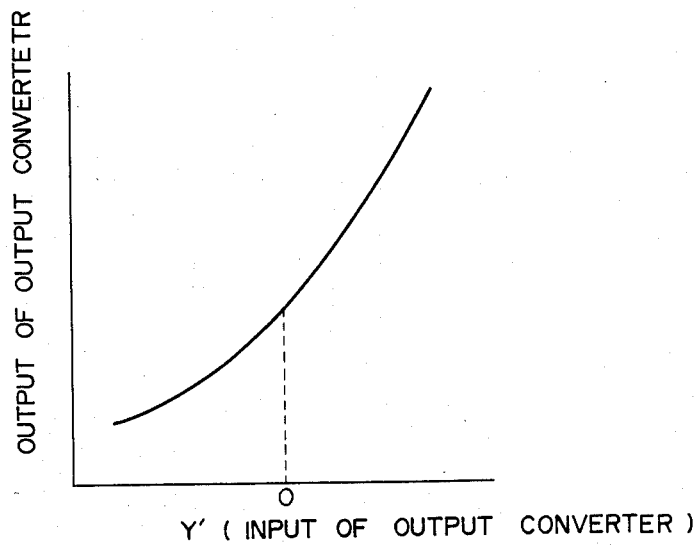
FIG. 20 is a graph showing a relation between the output and the input of an output converter.

Now, in a case where the impedance bridge 114 is so adjusted that Y' becomes zero when kept in the reference lift-off value, the output of phase rotation 150 is as shown by the broken line in FIG. 19. While, the flaw signal output caused by a change in the lift-off value decreases hyperbolically following an increase in the lift-off value. The signal output has been obtained by means of the artificial reference flaw as shown by the solid line in FIG. 19 and an output converter 151, as shown in FIG. 20, having the output characteristic changing reversely to the above with respect to the amount of lift-off variation has been provided, so that the output of phase rotator 150 is given to the output converter 151, resulting in that the output converter 151, when the lift-off value is larger, generates a signal of a high level, and when smaller, that of a low level. Such output of output converter 151 is given to a multiplier 152 which is given the output of first signal computing unit 130 as a multiplicand input, so that the output of signal computing unit 130, in turn the flaw signal, of the low (or high) level due to the larger (or smaller) lift-off value, is multiplied by the output of output converter 151 of high (or low) level, thereby becoming a signal depending not on the lift-off value, but on configurations of flaws.

Thus, the flaw detection apparatus of the invention combines the probe coils of standard comparison system, which has hitherto been considered not to be suitable for automatic flaw detection due to its large signal caused by the lift-off variation, with the multifrequency eddy current flaw detection technique effective in suppression of undesired signals, so that the suppression of signals caused by the lift-off variation, which has hitherto been not-operable with accuracy, and the correction of the flaw signal output changed by the lift-off variation, can simultaneously be carried out.

The probe coils of standard comparison type, as the abovementioned, have not generally been used as the flaw detection coils because they are affected largely by the lift-off, but the multifrequency method, when adopted, can detect the flaw signals only and also the lift-off amount itself can independently be measured as the output of phase rotator 150. Accordingly, in the above embodiment, the distance sensor 11 is used to obtain a distance between the probe 21 and the object 10, that is, the lift-off therebetween, which may alternatively obtain the lift-off by the probe itself, thereby controlling the center of the rotary drum 52 to be aligned with the center of the object 10.

As this invention may be embodied in several forms without departing from the spirit of essential characteristics thereof, the present embodiment is therefore illustrative and not restrictive, since the scope of the invention is defined by the appended claims rather than by the description preceeding them, and all changes that fall within meets and bounds of the claims, or equivalence of such meets and bounds are therefore intended to be embraced by the claims.

What is claimed is:

1. A flaw detection apparatus of rotary probe type which rotates a non contact probe at a spaced distance from the peripheral surface of a hot rolled object to be inspected that has a circular transverse cross-section, comprising:

a rotary member which supports and rotates said probe, a guide tube for guiding said object to be inspected toward the center of said rotary member, pinch rolls disposed before and after said rotary member, relative position changing means for changing the relative position of said rotary member with respect to said object to be inspected, distance detection means mounted on said rotary member for rotation therewith and continually operative to detect a distance between said probe and the peripheral surface of said object to be inspected and providing an output signal indicating said distance between said probe and said peripheral surface of said object, and means responsive to said output signal for controlling said relative position changing means to maintain a substantially constant spacing between said probe and said peripheral surface thereby to control lift-off errors during a flaw detection operation caused by variances in the distance between said probe and said object to be inspected.

2. A flaw detection apparatus as set forth in claim 1, wherein said probe is mounted to said rotary member by use of air cylinders, said air cylinders allowing said probe to move toward or away from said object to be inspected.

3. A flaw detection apparatus as set forth in claim 2, wherein compressed air for driving said air cylinders is supplied thereto through an outer annulus provided around said guide tube.

4. A flaw detection apparatus as set forth in claim 1, wherein said probe is provided with outlets through which a compressed fluid is to be blown out toward said object to be inspected.

5. A flaw detection apparatus as set forth in claim 4, wherein said compressed fluid is compressed air.

6. A flaw detection apparatus as set forth in claim 4, wherein said compressed fluid is supplied through an outer annulus provided around said guide tube.

7. A flaw detection apparatus as set forth in claim 1, wherein said guide tube is so constructed that a cooling medium is allowed to flow along the peripheral wall of said guide tube.

8. A flaw detection apparatus as set forth in claim 1, wherein said distance detection means comprises an eddy current system distance sensor.

9. A flaw detection apparatus as set forth in claim 1, wherein said probe comprises coils for carrying out eddy current flaw detection and serves also as said distance detection means.

10. A flaw detection apparatus as set forth in claim 1, wherein said control means for said relative position changing means averages the output signal from said distance detection means mounted to said rotary member as to a plural number of rotations thereof so that relative position change control is carried out in response to said average value from said process.

11. A flaw detection apparatus of rotary probe type which rotates a probe along the peripheral surface of a hot rolled object to be inspected that has a circular transverse cross-section, comprising:
a probe including first and second sensor coils,
a rotary member which supports said probe and rotates,
a guide tube for guiding said object to be inspected toward the center of said rotary member,
pinch rolls disposed before and after said rotary member,
relative position changing means for changing the relative position of said rotary member with respect to said object to be inspected,
distance detection means for detecting a distance between said probe and the peripheral surface of said object to be inspected and providing an output signal indicating said distance between said probe and said peripheral surface of said object,
control means responsive to said output signal for controlling said relative position changing means
means for applying to said first and second coils a mixed signal of a plurality of frequencies, said coils providing a signal indicating the impedance of the coils, said impedance being a function of the distance between said probe and said peripheral surface of said object to be inspected,
first signal computing means operative in response to said coil impedance signals for removing the signal component of one of said coil impedance signals caused by variation in the distance between said probe and said peripheral surface of said object to be inspected,
second signal computing means operative in response to said coil impedance signals for detecting the signal component of one of said coil impedance signals caused by variation in the distance between said probe and said peripheral surface of said object to be inspected, and
means operative in response to an output from said second signal computing means for adjusting an output of said first signal computing means such that the adjusted output signal of said first computing means provides an indication of flaws present in said object to be inspected.

12. A flaw detection apparatus as set forth in claim 11, wherein said probe is mounted to said rotary member by use of air cylinders, said air cylinders allowing said probe to move toward or away from said object to be inspected.

13. A flaw detection apparatus as set forth in claim 12, wherein compressed air for driving said air cylinders is supplied thereto through an outer annulus provided around said guide tube.

14. A flaw detection apparatus as set forth in claim 11, wherein said probe is provided with outlets through which a compressed fluid is to be blown out toward said object to be inspected.

15. A flaw detection apparatus as set forth in claim 14, wherein said compressed fluid is compressed air.

16. A flaw detection apparatus as set forth in claim 14, wherein said compressed fluid is supplied through an outer annulus provided around said guide tube.

17. A flaw detection apparatus as set forth in claim 11, wherein said guide tube is so constructed that a cooling medium is allowed to flow along the peripheral wall of said guide tube.

18. A flaw detection apparatus as set forth in claim 11, wherein said distance detection means comprises an eddy current system distance sensor.

19. A flaw detection apparatus as set forth in claim 11, wherein said probe comprises coils for carrying out eddy current flaw detection and serves also as said distance detection means.

20. A flaw detection apparatus as set forth in claim 11, wherein said control means for said relative position changing means averages said output signal from said distance detection means mounted to said rotary member as to a plural number of rotations thereof so that relative position change control is carried out in response to the average value from said process.

* * * * *